United States Patent [19]

Sato et al.

[11] 4,338,251

[45] Jul. 6, 1982

[54] TWO-FUNCTIONAL-GROUP-CONTAINING TERPENOIDS, PROCESSES FOR THE PREPARATION OF THE SAME, AND ANTI-ULCER AGENTS CONTAINING THE SAME

[75] Inventors: Akio Sato, Yatabe; Kenji Nakajima, Sakuramura; Yoshimasa Takahara, Narashino; Shizumasa Kijima, Niiza; Noriaki Kuwana, Aichi; Shinya Abe, Kawagoe; Kouzi Yamada, Tokyo, all of Japan

[73] Assignees: Eisai Co., Ltd.; Agency of Industrial Science and Technology, both of Tokyo, Japan; a part interest to each

[21] Appl. No.: 221,163

[22] Filed: Dec. 29, 1980

[30] Foreign Application Priority Data

Jan. 12, 1980 [JP] Japan ................................. 55-2395

[51] Int. Cl.³ .............................................. C09E 5/00
[52] U.S. Cl. ............................. 260/405.5; 260/456 R; 568/857; 568/662; 568/598; 568/497; 568/442; 424/312; 424/314; 435/134; 549/420; 549/423
[58] Field of Search ...................... 260/345.9 R, 405.5, 260/456 R, 345.7 R; 568/857, 662, 598, 442, 497

[56] References Cited

PUBLICATIONS

Kjøsen et al., ACTA Chem. Scand., 26, 4121–4129, (1972).
Sakagami et al., Agric. Biol. Chem., 43, 2643, (1979).

*Primary Examiner*—Nicky Chan
*Attorney, Agent, or Firm*—Blanchard, Flynn, Thiel, Boutell & Tanis

[57] ABSTRACT

A process for the preparation of a two-functional-group-containing terpenoid having the general formula:

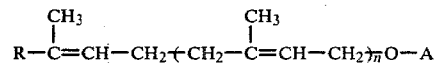

in which n is an integer of from 1 to 5, R represents a hydroxymethyl, formyl or carboxyl group, and A represents the hydrogen atom, or a 2-tetrahydropyranyl, benzyl, methoxymethol or methoxyethoxymethyl group comprising the oxidation with a microorganism belonging to the genus Nocardia. Some of the terpenoids are of value as anti-ulcer agents, while others are useful as intermediates.

4 Claims, No Drawings

TWO-FUNCTIONAL-GROUP-CONTAINING TERPENOIDS, PROCESSES FOR THE PREPARATION OF THE SAME, AND ANTI-ULCER AGENTS CONTAINING THE SAME

This invention relates to terpenoids containing two functional groups and having the general formula (I):

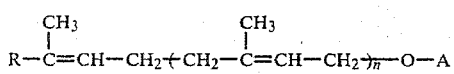

in which n is an integer of from 1 to 5, R represents a hydroxymethyl, formyl or carboxyl group, and A represents hydrogen, or a 2-tetrahydropyranyl, benzyl, methoxymethyl or methoxyethoxymethyl group, provided that when A is one of the groups other than hydrogen, R represents a carboxyl group, a process for the preparation of such terpenoids by oxidation of a compound having the formula (I) wherein R is methyl and A is 2-tetrahydropyranyl, benzyl, methoxymethyl or methoxyethoxymethyl, with a microorganism, and an anti-ulcer composition containing such a terpenoid.

Japanese Patent Provisional Publication Nos. 54(1979)-70430 and 54(1979)-76513 respectively describe that certain chain structure-type (acyclic) terpenoids containing a hydroxyl group at one terminal and esters of such terpenoids have a hypotensive activity.

According to this invention, it has been found that a compound of the general formula (I), in which A is hydrogen, is effective as an anti-ulcer agent.

According to another aspect of this invention, it has been found that a compound of the general formula (I) is of value as an intermediate for the preparation of pharmaceutically active compounds, such as a polyprenyl alcohol.

The polyprenyl alcohol is of value, from one aspect, as a hypotensive agent, and is also of value for forming the side-chain of the pharmaceutically active coenzyme Q. The polyprenyl alcohol can be prepared from a compound of the general formula (I) in which R is the hydroxymethyl group, and A is a protecting group for the hydroxyl group such as a 2-tetrahydropyranyl, benzyl, methoxymethyl or methoxyethoxymethyl group, via the carbon chain prolonging reaction illustrated below:

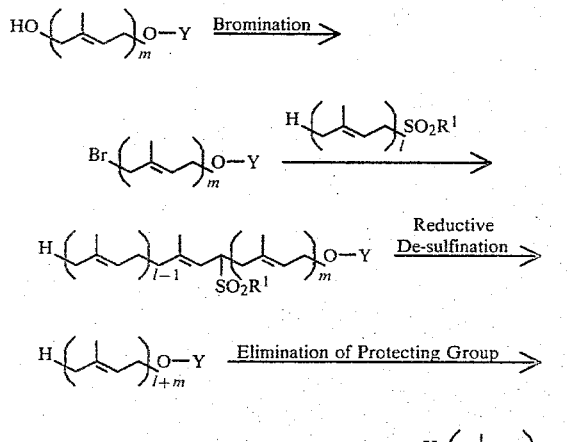

In the above equations, l and m are integers and Y represents the protecting group for the hydroxyl group. $R^1$ is a $C_1$-$C_4$ alkyl or aryl such as benzene and toluene.

Accordingly, a compound of the general formula (I) can be used, per se, as an intermediate for preparing the polyprenyl alcohol, provided that in the starting compound of the general formula (I), R represents the hydroxymethyl group and A represents a 2-tetrahydropyranyl, benzyl, methoxymethyl or methoxyethoxymethyl group. A compound of the general formula (I) in which R represents a formyl or carboxyl group and/or A represents hydrogen can be also used as the intermediate if the formyl or carboxyl group is reduced to form the hydroxymethyl group and/or the hydrogen atom is protected by an appropriate protecting group.

As for a process for oxidizing a terminal group of a chain structure-type terpenoid having a functional group at the other terminal, it is disclosed in Japanese Patent Provisional Publication No. 53(1978)-103445 that a chain structure terpenoid having at one terminal a hydroxyl group protected by a protecting group is oxidized by the use of selenium oxide to change the other terminal group into a formyl group and then is reduced. This process, however, shows a poor yield in the oxidation step. This tendency is prominent, particularly on the reaction of a compound having a longer carbon atom chain. Further, it is noted that the oxidizing step inherently yields an organic selenium compound as a by-product. The separation of the thus-produced by-product from the desired compound is very difficult even by a method such as column chromatography or distillation. The organic selenium compound is known to be toxic to human beings. Therefore, the above-mentioned process is not preferable as a process for the preparation of an intermediate for synthesizing a pharmaceutically active compound.

In view of the above-described problem, the present inventors studied a process utilizing a microorganism and discovered that a microorganism oxidation, utilizing a microorganism belonging to the genus Nocardia, can be employed for the preparation of the desired compound, thereby eliminating the above-described problem. The present process utilizing the Nocardia microorganism enables the mass production of the desired compound by enlarging the size of the cultivating system. Moreover the unreacted reactant can be readily recovered and then reused as the starting reactant.

A representative strain among those belonging to the genus Nocardia and which is advantageously employed in the present invention is one named BPM 1613 that has been deposited with the Fermentation Research Institute, the Agency of Industrial Science and Technology at 1-1-3, Higashi, Tsukuba-Yatabe-machi, Ibaraki-prefecture, Japan, and has been added to its collection of microorganisms under the designation FERM-P No. 1609. The mycological characteristics of the representative strain named BPM 1613 are given below. The color is expressed according to the "Color Standard" published by Nippon Shikisai Kenkyusho (Japan Color Research Center), Japan.

A. Form of Cells

The present strain shows a characteristic orange to pink color in almost all culture media, as seen from the following cultural characteristics. A young vegetative cell grows in a myceloid form, and branching is rarely observed. In an aged cultivated system, the hypha is divided to form a bacillus (0.4–0.6×1.8–2.4 mm). Gram positive. No flagellum. Negative on the acid-fast stain according to the Ziehl-Neelsen method. Aerial mycelium is not observed.

B. Cultural Characteristics on Various Media
(1) Sucrose—Nitrate Agar Medium (30° C.): poor growth, pink colored colony, no diffusive pigment
(2) Glucose—Asparagine Agar Medium (30° C.): no growth
(3) Glycerol—Asparagine Agar Medium (30° C.): poor growth, pink colored colony, no diffusive pigment
(4) Starch Agar Medium (30° C.): no growth
(5) Tyrosine Agar Medium (30° C.): poor growth, grayish white colored colony, no diffusive pigment
(6) Nutrient Agar Medium (30° C.): moderate growth, orange colored colony, no diffusive pigment
(7) Yeast—Malt Agar Medium (30° C.): rich growth, orange colored colony, no diffusive pigment
(8) Oatmeal Agar Medium (30° C.): moderate growth, orange colored colony, no diffusive pigment
(9) Calcium Malate Agar Medium (27° C.): moderate growth, pink colored colony
(10) Egg-albumin Medium (slant, 27° C.): poor growth, white colony
(11) Potato Section Medium (27° C.): moderate growth, pale orange colored colony
(12) Carrot Section Medium (27° C.): moderate growth, pale orange colored colony C. Physiological Characteristics
(1) Growth Temperature Range (on Nutrient Agar Medium, slant): 20°–42° C.
(2) Liquefaction of Gelatin: negative
(3) Hydrolysis of Starch: negative
(4) Coagulation of Defatted Milk, Peptonization: negative
(5) Litmus Milk: no change
(6) Production of Melanine-like pigment: negative
(7) Reduction of Nitrate: positive
(8) No gas or acid production from L-arabinose, D-xylose, D-glucose, D-fructose, sucrose, D-mannitol, glycerol, lactose, D-galactose, D-mannose, maltose, trehalose, starch
(9) Catalase Test: negative
(10) Production of Indole: negative
(11) Production of Hydrogen Sulfide: negative D. Assimilability for Various Carbon Sources
(Pridham-Gottlieb Agar Medium, 30° C., 7 days)
L-arabinose (+), D-xylose (+), D-glucose (++), D-fructose (++), sucrose (++), inositol (+), L-rhamnose (−), raffinose (+), D-mannitol (+)
(In the above, (++) means moderate growth, (+) poor growth, and (−) no growth.)

The above-identified strain having been cultivated on the Glycerol Kelner Morton Medium in accordance with the method of Arai et al described in Journal of General Applied Microbiology, 9, 119 (1963): The Actinomycetales, The Jena International Symposium on Taxonomy, 273 (1968) gives absorption bands characteristic of the genus Nocardia on the IR spectrum, that is, I: C & E types, II: C type, III: C type, IV: D type.

Upon studying the above-described characteristics of the strain with reference to Bergey's Manual of Determinative Bacteriology, Seventh edition, and Waksman's The Actinomycetes, Volumn 2, the strain is determined to belong to the genus Nocardia.

A process for the preparation of the compound of the present invention is described hereinbelow.

In the first stage, a microorganism belonging to the genus Nocardia and showing an oxidizing activity for a compound having the general formula (II):

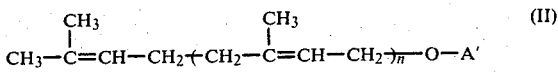

in which A' represents a 2-tetrahydropyranyl, benzyl, methoxymethyl or methoxyethoxymethyl group, and n is an integer of from 1 to 5, is cultivated in a culture medium containing a compound of the general formula (II) as the carbon source. Then, the thus-produced compound having the general formula (III):

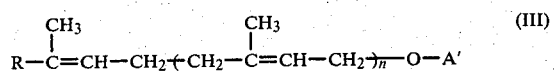

in which R represents a hydroxymethyl, formyl or carboxyl group, and n and A' have the same meanings as defined above, is recovered from the culture medium. Finally, the protecting group is eliminated from the compound of the general formula (III) to obtain a compound having the general formula (IV):

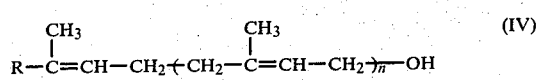

in which R and n have the same meanings as defined above.

There is no specific limitation on the microorganism of the present invention belonging to the genus Nocardia, provided that it has an oxidizing activity for a compound of the general formula (II). Examples of these microorganisms include the strain of BPM 1613, FERM-P No. 1609, as specified hereinbefore.

Details of the cultivating procedures are as follows.

In addition to the compound of the general formula (II) included as the carbon source, sources of other nutrients for the cultivation can be selected from conventional ones. As the nitrogen source, there can be mentioned nitrates such as potassium nitrate, sodium nitrate, and ammonium nitrate, ammonium salts such as ammonium chloride, ammonium sulfate and ammonium phosphate, ammonia, and urea. Other inorganic salts such as potassium phosphate, sodium phosphate, magnesium sulfate, ferric sulfate and manganese sulfate, and other organic nutrient sources such as vitamins, amino acids, and yeast extracts, corn steep liquors and malt extracts containing these nutrients can be further incorporated in the medium, if necessary. The medium is preferably adjusted to be alkaline, for instance, in the range of pH 7–10. The cultivation is conveniently carried out at 20°–40° C., for 3–5 days, and under an aerobic condition, such as by effecting the cultivation with aeration and stirring.

Upon completion of the cultivation, the cultivated medium is extracted with an organic solvent to recover a compound of the general formula (III). As the extracting solvent, there can be employed ethyl ether, benzene, chloroform, etc. The compound of the general formula (III) can be separated and purified on a column of silica gel.

The unreacted reactants can be recovered through the above-mentioned extracting procedure and column chromatography, in approximately 80–90% recovery, and employed again as the reactants for another cycle.

The compound having a hydroxymethyl, formyl or carboxyl group at the terminal can be obtained depending upon the extent of the microbiological oxidation. Further, the configuration of the resulting product can be varied by varying the cultivating conditions, the protecting group of the hydroxyl group of the starting compound, etc.

The elimination of the protecting group from a compound of the general formula (III) can be carried out in a conventional manner, depending on the protecting group to be eliminated. For instance, the tetrahydropyranyl, methoxymethyl and methoxyethoxymethyl groups can be eliminated under an acidic condition, and the benzyl group can be eliminated under a reductive condition.

The results of the pharmacological and toxicity tests on the compound of the present invention are set forth below.

(1) Effect on Cold-Restaint Stress Ulcer

The inhibition effect of the test compound on the cold-restaint stress ulcer was determined according to the Levine' method [Proc. Soc. Exptl. Biol. Med., Vol. 124, Page 1221 (1967)] using rats (SD family, female, weight about 170 g, 8–10 weeks age). The test compounds are set forth below.

12-Hydroxy-2,6,10-trimethyl-2,6,10-dodecatrienoic acid—(Compound A)

2,6,10,14-Tetramethyl-2,6,10,14-hexadecatetraene-1,16-diol—(Compound B)

16-Hydroxy-2,6,10,14-tetramethyl-2,6,10,14-hexadecatetraenoic acid—(Compound C)

20-Hydroxy-2,6,10,14,18-pentamethyl-2,6,10,14,18-eicosapentaenoic acid—(Compound D)

The inhibition ratios on the occurrence of the cold restrictive stress ulcer obtained by the present procedures are set forth in Table 1.

TABLE 1

| Test Compound | Inhibition Ratio (%) |
|---|---|
| Compound A | 74.6 |
| Compound B | 70.8 |
| Compound C | 79.2 |
| Compound D | 49.5 |

(2) Toxicity Test

Each of the compounds B and C was administered orally to a rat (SD family, female, weight about 200 g) in the dosage of 5,000 mg/Kg. No death was observed for each test.

As is apparent from these pharmacological and toxicity tests, the compound of the present invention is of value as an anti-ulcer agent. When the compound of the invention is intended to be used as an anti-ulcer agent, it is generally administered orally or parenterally to a human being in the dosage of 50–1,000 mg/day, for an adult. The administration is conventionally performed in the form of granules, tablets, capsules or injectable solutions. These pharmaceutical unit dosage forms can be prepared in a conventional manner using conventional pharmaceutical carriers.

The present invention is further described by reference to the following illustrative Examples.

EXAMPLE

Preparation of Starting Compound $$CH_3-\underset{\underset{CH_3}{|}}{C}=CH-CH_2+CH_2-\underset{\underset{CH_3}{|}}{C}=CH-CH_2\overline{)_n}-O-A'$$

(1) Tetrahydropyranyl ether (A' = tetrahydropyranyl)

In methylene chloride were dissolved 15 g of 3,7,11,15-tetramethyl-2,6,10,14-hexadecatetraen-1-ol and 1.5 g of p-toluenesulfonic acid, and to the solution was dropwise added, under stirring, 8.7 g of 2,3-dihydropyran, at 0°–5° C. and over a period of 30 min. The resulting solution was further stirred at 0°–5° C. for 30 min., and then washed with an aqueous sodium carbonate solution in a separatory funnel. The solution was concentrated after the washing, and the concentrated solution was purified over a silica gel column to give 13 g of 1-(2-tetrahydropyranyl)oxy-3,7,11,15-tetramethyl-2,6,10,14-hexadecatetraene (yield 68%).

Other tetrahydropyranyl ethers were prepared in the same manner as described above.

(2) Benzyl ether (A' = benzyl)

To 100 ml of benzyl chloride were added 15 g of 3,7,11,15-tetramethyl-2,6,10,14-hexadecatetraen-1-ol and 6.0 g of finely divided potassium hydroxide, and the resulting mixture was refluxed under stirring for 2 hours. The mixture was cooled and then to the mixture was added 1 liter of hexane. The hexane solution was then washed with water and concentrated. The concentrate was purified over a silica gel column to give 12 g of 1-benzyloxy-3,7,11,15-tetramethyl-2,6,10,14-hexadecatetraene (yield 61%).

Other benzyl ethers were prepared in the same manner as described above.

The yields and NMR spectral data of the thus-obtained tetrahydropyranyl and benzyl ethers are summarized in Table 2.

TABLE 2

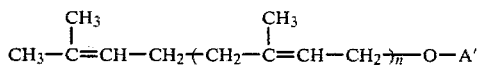

$$CH_3-\underset{\underset{CH_3}{|}}{C}=CH-CH_2+CH_2-\underset{\underset{CH_3}{|}}{C}=CH-CH_2\overline{)_n}-O-A'$$

| n | A' | Yield (%) | NMR (δ, CDCl₃) |
|---|---|---|---|
| 1 | (tetrahydropyranyl) | 82 | 1.22~1.84 (6H), 1.61 (3H, s), 1.68 (6H, s), 1.84~2.31 (4H), 3.35~4.36 (4H), 4.61 (1H, b r), 5.11 (1H, b r), 5.36 (1H, t, J = 7) |
| 2 | (tetrahydropyranyl) | 76 | 1.20~1.84 (6H), 1.61 (6H, s), 1.68 (6H, s), 1.84~2.32 (8H), 3.32~4.36 (4H), 4.61 (1H, b r), 5.10 (2H, b r), 5.35 (1H, t, J = 7) |

TABLE 2-continued $$CH_3-\underset{\underset{CH_3}{|}}{C}=CH-CH_2-(CH_2-\underset{\underset{CH_3}{|}}{C}=CH-CH_2)_{\overline{m}}-O-A'$$

| n | A' | Yield (%) | NMR (δ, CDCl₃) |
|---|----|-----------|----------------|
| 3 | (tetrahydropyranyl) | 68 | 1.13~1.80 (6H), 1.62 (9H, s), 1.70 (6H, s), 1.80~2.30 (12H), 3.40~4.35 (4H), 4.60 (1H, b r), 5.12 (3H, b r), 5.38 (1H, t, J = 7) |
| 4 | (tetrahydropyranyl) | 71 | 1.21~1.80 (6H), 1.62 (12H, s), 1.69 (6H, s), 1.78~2.28 (16H), 3.38~4.36 (4H), 4.61 (1H, b r), 5.11 (4H, b r), 5.36 (1H, t, J = 7) |
| 5 | (tetrahydropyranyl) | 78 | 1.32~1.76 (6H), 1.60 (15H, s), 1.68 (6H, s), 1.78~2.32 (20H), 3.32~4.36 (4H), 4.61 (1H, b r), 5.10 (5H, b r), 5.35 (1H, t, J = 7) |
| 2 | —CH₂—C₆H₅ | 85 | 1.59 (6H, s), 1.65 (6H, s), 1.80~2.30 (8H), 4.01 (2H, d, J = 7), 4.49 (2H, s), 5.10 (2H, b r), 5.39 (1H, J = 7), 7.08~7.42 (5H) |
| 3 | —CH₂—C₆H₅ | 61 | 1.63 (9H, s), 1.68 (6H, s), 1.82~2.30 (12H), 4.05 (2H, d, J = 7), 4.55 (2H, s), 5.16 (3H, b r), 5.46 (1H, t, J = 7), 7.10~7.45 (5H) |
| 4 | —CH₂—C₆H₅ | 88 | 1.61 (12H, s), 1.67 (6H, s), 1.80~2.30 (16H), 4.03 (2H, d, J = 7), 4.51 (2H, s), 5.13 (4H, b r), 5.40 (1H, t, J = 7), 7.12~7.47 (5H) |

EXAMPLE 1

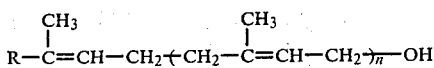

$$R-\underset{\underset{CH_3}{|}}{C}=CH-CH_2-(CH_2-\underset{\underset{CH_3}{|}}{C}=CH-CH_2)_{\overline{m}}-OH$$

(a) Microbiological oxidation

On 50 ml of a medium (pH 7.2) containing 1% of the compound prepared in the aforementioned example for the preparation of starting compound, 0.25% of NH₄NO₃, 0.15% of KH₂PO₄, 0.15% of Na₂HPO₄, 0.05% of MgSO₄.7H₂O, 0.001% of FeSO₄.7H₂O, 0.001% of CaCl₂.2H₂O and 0.002% of yeast extract was inoculated, in an 8% volume ratio, a culture solution in which the strain belonging to the genus Nocardia (BPM-1613, FERM-P No. 1609) had been shaken-cultivated at 30° C. for 2 days on a culture medium (the latter medium having the same composition as the first-mentioned medium defined above, except that 1% of the starting compound had been replaced with 0.5% of n-paraffin). The thus-inoculated medium was shaken-cultivated at 30° C. for 5 days in a 500 ml volume shouldered flask. After the cultivation was complete, the medium was extracted with diethyl ether under acidic condition (ph 2) of sulfuric acid. The solvent was then evaporated, and the residue was purified over a silica gel column. The development was carried out with hexane and diethyl ether.

The products obtained in the above-described manner are set forth in Table 3, together with data such as physical condition, yield, mass spectrum and NMR spectrum. The products obtained by the oxidation were observed to be mixtures of the alcohol, aldehyde and carboxylic acid, according to the silica gel thin layer chromatographic data. In Table 3, the main products only are set forth. The NMR spectral data for the carboxylic acids are set forth based on the measurement on methyl esters of the carboxylic acids.

TABLE 3

$$R-\underset{\underset{CH_3}{|}}{C}=CH-CH_2-(CH_2-\underset{\underset{CH_3}{|}}{C}=CH-CH_2)_{\overline{m}}-O-A'$$

| n | A' | R | Physical State Yield (%) | Mass (M+) | NMR (δ, CDCl₃) |
|---|----|----|--------------------------|-----------|----------------|
| 1 | (tetrahydropyranyl) | HOOC— | Oil 8.00 | 268 | (as methyl ester) 1.40~1.75 (6H), 1.70 (3H, s), 1.83 (3H, s), 2.06~2.50 (4H), 3.36~4.36 (4H), 4.63 (1H, br), 5.39 (1H, t, J = 7), 6.87 (1H, t, J = 7), 10.48 (1H, br) |
|   | (tetrahydropyranyl) | OHC— | Oil 1.2 | 252 | 1.40~1.88 (6H), 1.68 (3H, s), 1.75 (3H, s), 1.96~2.36 (4H), 3.37~4.32 (4H), 4.60 (1H, br), 5.30 (1H, t, J = 7), 6.46 (1H, t, J = 6), 9.38 (1H, s) |
| 2 | (tetrahydropyranyl) | HOOC— | Oil 4.36 | 336 | (as methyl ester) 1.20~1.90 (6H), 1.60 (3H, s), 1.68 (3H, s), 1.84 (3H, s), 1.90~2.40 (8H), 3.32~4.35 (4H), 3.73 (3H, s), 4.60 (1H, br), 5.12 (1H, br), 5.35 (1H, t, J = 7), 6.72 (1H, t, J = 7) |
| 3 | (tetrahydropyranyl) | HOH₂C— | Oil 14.2 | 390 | 1.20~1.82 (6H), 1.62 (6H, s), 1.68 (3H, s), 1.80~2.28 (3H), 3.38~4.37 (4H), 3.97 (2H, s), 4.63 (1H, br), 5.12 (2H, br), 5.37 (2H, br) |
|   | (tetrahydropyranyl) | HOOC— | Oil 19.6 | 404 | (as methyl ester) 1.35~1.80 (6H), 1.60 (6H, s), 1.70 (3H, s), 1.84 (3H, s), 1.92~2.43 (12H), 3.36~4.40 (4H), 4.62 (1H, br), 5.12 (2H, br), 5.37 (1H, t, J = 7), 6.86 (1H, t, J = 7), 10.60 (1H, br) |

TABLE 3-continued $$R-C(CH_3)=CH-CH_2+(CH_2-C(CH_3)=CH-CH_2)_{\overline{n}}-O-A'$$

| n | A' | R | Physical State Yield (%) | Mass (M+) | NMR (δ, CDCl₃) |
|---|---|---|---|---|---|
| 4 |  | HOOC— | Oil 22.6 | 472 | (as methyl ester) 1.30~1.80 (6H), 1.62 (9H, s), 1.69 (3H, s), 1.84 (3H, s), 1.90~2.45 (16H), 3.37~4.38 (4H), 4.64 (1H, br), 5.12 (3H, br), 5.37 (1H, t, J = 7), 6.89 (1H, t, J = 7), 10.82 (1H, br) |
|   |   | HOH₂C— | Oil 14.8 | 458 | 1.20~1.85 (6H), 1.62 (9H, s), 1.68 (6H, s), 1.85~2.40 (17H), 3.35~4.36 (4H), 3.97 (2H, s), 4.62 (1H, br), 5.12 (3H, br), 5.37 (2H, br) |
| 5 |  | HOOC— | Oil 1.17 | 540 | (as methyl ester) 1.30~1.76 (6H), 1.58 (12H, s), 1.68 (3H, s), 1.83 (3H, s), 1.87~2.32 (20H), 3.36~4.36 (4H), 3.73 (3H, s), 4.61 (1H, br), 5.10 (4H, br), 5.35 (1H, t, J = 7), 6.72 (1H, t, J = 7) |
|   |   | HOH₂C— | Oil 1.06 | 526 | 1.12~1.79 (6H, br), 1.61 (12H, s), 1.68 (6H, s), 1.78~2.32 (21H), 3.30~4.40 (4H), 3.97 (2H, s), 4.61 (1H, br), 5.10 (4H, br), 5.35 (2H, t, J = 7) |
| 2 | 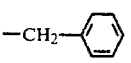 —CH₂— | HOOC— | Oil 3.33 | 342 | (as methyl ester) 1.61 (3H, s), 1.64 (3H, s), 1.82 (3H, s), 1.96~2.40 (8H), 3.72 (3H, s), 4.01 (2H, d, J = 7), 4.49 (2H, s), 5.12 (1H, t, J = 7), 5.38 (1H, t, J = 7), 6.71 (1H, t, J = 7), 7.04~7.42 (5H) |
| 3 | 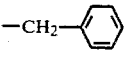 —CH₂— | HOOC— | Oil 14.2 | 410 | (as methyl ester) 1.62 (6H, s), 1.65 (3H, s), 1.83 (3H, s), 1.90~2.42 (12H), 3.73 (3H, s), 4.03 (2H, d, J = 7), 4.52 (2H, s), 5.12 (2H, br), 5.36 (1H, t, J = 7), 6.87 (1H, t, J = 7), 7.05~7.45 (5H) |
| 4 | 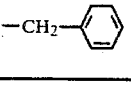 —CH₂— | HOOC— | Oil 16.8 | 478 | (as methyl ester) 1.61 (9H, s), 1.65 (3H, s), 1.84 (3H, s), 1.92~2.40 (16H), 3.75 (3H, s), 4.01 (2H, d, J = 7), 4.51 (2H, s), 5.12 (3H, br), 5.36 (1H, t, J = 7), 6.81 (1H, t, J = 7), 7.00~7.46 (5H) |

(b) Elimination of protecting group (1) Tetrahydropyranyl ether

To 6 ml of pyridine was added 2.35 g of p-toluene-sulfonic acid, and the mixture was stirred at room temperature for 20 min. The solvent was evaporated, and the residue was washed with acetone and dissolved in water (3.15 mg/ml). To 100 mg of the 20-(2-tetrahydropyranyl)-oxy-2,6,10,14,18-pentamethyl-2,6,10,14,18-eicosapentaenoic acid obtained as described in the previous (a) section was added 4 ml of the aqueous solution obtained as described above. The mixture was then stirred at 55° C. for 3 hours, and cooled. Then the mixture was extracted with 50 ml of diethyl ether, and the extract was evaporated to remove the solvent, giving 82 mg of 20-hydroxy-2,6,10,14,18-pentamethyl-2,6,10,14,18-eicosapentaenoic acid.

Other tetrahydropyranyl ethers obtained in the previous (a) section were treated in the same manner to eliminate the protecting groups.

(2) Benzyl ether

To 150 ml of ethylamine was added piece by piece 1.7 g of wire-shaped metallic lithium (containing 1% sodium) at −78° C. in a nitrogen stream. The mixture was left to reach −20° C. so as to dissolve the added lithium metal completely therein. Subsequently, the solution was again cooled to −78° C.

In 50 ml of tetrahydrofuran was dissolved 5 g of the 16-benzyloxy-2,6,10,14-tetramethyl-2,6,10,14-hexadecatetraenoic acid obtained as described in the previous (a) section. This solution was added dropwise to the above-prepared lithium solution over a period of 30 min. The mixture was stirred for 30 min., and 1,3-butadiene was introduced into the mixture until the color of the mixture (blue) faded. To the resulting yellow colored solution was added methanol until the yellow faded. Subsequently, this was left standing to reach room temperature. The solid product thus obtained was collected on a filter, and then dissolved in water. The aqueous solution was made weakly-acidic by addition of 1 N hydrochloric acid under ice-cooling, and then extracted with hexane. The extract was washed successively with water and a saturated aqueous sodium chloride solution, and then dried over magnesium sulfate. The dried extract was concentrated, and the thus-obtained concentrate was purified over a silica gel column to give 3.3 g of 16-hydroxy-2,6,10,14-tetramethyl-2,6,10,14-hexadecatetraenoic acid.

Other benzyl ethers obtained as described in the previous (a) section were treated in the same manner to eliminate the protecting groups.

The products obtained in the above-described manner are set forth in Table 4, together with data such as physical state, yield, mass spectrum and NMR spectrum. In Table 4, the yields with the * mark indicate yields for the reactions of eliminating the protecting groups from the benzyl ethers obtained in the above (2) section, while the yields with no mark indicate yields for the reactions of eliminating the protecting groups from the tetrahydropyranyl ethers obtained in the above (1) section.

TABLE 4

$$R-\underset{\underset{CH_3}{|}}{C}=CH-CH_2+CH_2-\underset{\underset{CH_3}{|}}{C}=CH-CH_2\overline{)_m}-OH$$

| n | R | Physical State Yield (%) | Mass (M+) | NMR (δ, CDCl₃) |
|---|---|---|---|---|
| 1 | HOOC— | Oil 98 | 184 | 1.69 (3H, s), 1.84 (3H, s), 2.02~2.50 (4H, m), 4.18 (2H, d, J = 7), 5.32 (1H, t, J = 7), 6.86 (1H, t, J = 6), 7.02 (2H, br) |
| 1 | OHC— | Oil 99 | 168 | 1.67 (3H, s), 1.75 (3H, s), 1.96~2.30 (5H, m), 4.20 (2H, d, J = 7), 5.30 (1H, t, J = 7), 6.46 (1H, t, J = 6), 9.50 (1H, s) |
| 2 | HOOC— | Oil 96 *77 | 252 | 1.62 (3H, s), 1.69 (3H, s), 1.84 (3H, s), 1.90~2.40 (8H), 4.14 (2H, d, J = 7), 5.12 (1H, t, J = 6), 5.42 (1H, t, J = 7), 6.80 (2H, br), 6.87 (1H, t, J = 6) |
| 3 | HOH₂C— | Oil 96 | 306 | 1.60 (6H, s), 1.67 (6H, s), 1.92~2.45 (14H), 3.97 (2H, s), 4.16 (2H, d, J = 7), 5.10 (2H, br), 5.40 (2H, br) |
| 3 | HOOC— | Oil 97 *85 | 320 | 1.60 (6H, s), 1.67 (3H, s), 1.83 (3H, s), 1.90~2.40 (12H), 4.15 (2H, d, J = 7), 5.10 (2H, br), 5.41 (1H, t, J = 7), 6.76 (2H, br), 6.85 (1H, t, J = 6) |
| 4 | HOOC— | Oil 100 *82 | 388 | 1.60 (9H, s), 1.67 (3H, s), 1.83 (3H, s), 1.87~2.44 (16H), 4.14 (2H, d, J = 7), 5.10 (3H, br), 5.40 (1H, t, J = 7), 6.80 (2H, br), 6.86 (1H, t, J = 6) |
| 4 | HOH₂C— | Oil 97 | 374 | 1.62 (9H, s), 1.67 (6H, s), 1.87~2.35 (18H), 3.98 (2H, s), 4.15 (2H, d, J = 7), 5.11 (3H, br), 5.40 (2H, br) |
| 5 | HOOC— | Oil 98 | 456 | 1.61 (12H, s), 1.68 (3H, s), 1.83 (3H, s), 1.83~2.40 (20H), 4.13 (2H, d, J = 7), 5.10 (4H, br), 5.42 (1H, t, J = 7), 6.80 (2H, br), 6.86 (1H, t, J = 6) |
| 5 | HOH₂C— | Oil 97 | 442 | 1.61 (12H, s), 1.68 (6H, s), 1.76~2.32 (22H), 3.96 (2H, s), 4.13 (2H, d, J = 7), 5.10 (4H, br), 5.42 (2H, br) |

EXAMPLE 2

| Capsule | |
|---|---|
| 16-Hydroxy-2,6,10,14-tetramethyl-2,6,10,14-hexadecatetraenoic acid | 5 g |
| Micro-crystalline cellulose | 80 g |
| Corn starch | 20 g |
| Lactose | 22 g |
| Polyvinylpyrolidone | 8 g |

The above-listed components were granulated in a conventional manner and filled in a gelatine hard capsule. One capsule contained 10 mg of the principal active agent.

The embodiments of the invention in which an exclusive property or privilege is claimed are defined as follows:

1. The compound 12-hydroxy-2,6,10-trimethyl-2,6,10-dodecatrienoic acid

2. The compound 16-hydroxy-2,6,10,14-tetramethyl-2,6,10,14-hexadecatetraenoic acid.

3. The compound 20-hydroxy-2,6,10,14,18-pentamethyl-2,6,10,14,18-eicosapentaenoic acid.

4. The compound 24-hydroxy-2,6,10,14,18,22-hexamethyl-2,6,10,14,18,22-tetracosahexaenoic acid.

* * * * *

UNITED STATES PATENT AND TRADEMARK OFFICE
CERTIFICATE OF CORRECTION

PATENT NO. : 4 338 251
DATED : July 6, 1982
INVENTOR(S) : Akio SATO et al

It is certified that error appears in the above-identified patent and that said Letters Patent is hereby corrected as shown below:

Column 2, last line; change "mm" to ---μm---.

Signed and Sealed this

Twenty-third Day of December, 1986

Attest:

DONALD J. QUIGG

Attesting Officer    Commissioner of Patents and Trademarks